United States Patent
Seitz et al.

(10) Patent No.: US 8,304,504 B2
(45) Date of Patent: Nov. 6, 2012

(54) CATALYST PRECURSOR FOR THE PRODUCTION OF OLEFINS WITH AN ODD NUMBER OF CARBONS ATOMS, PROCESS FOR ITS PREPARATION AND PRODUCTION METHOD FOR SUCH OLEFINS

(75) Inventors: Marcus Seitz, Bayreuth (DE); Helmut G. Alt, Bayreuth (DE); Syriac J. Palackal, Munich (DE); Atieh Abu-Raqabah, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 694 days.

(21) Appl. No.: 11/919,147

(22) PCT Filed: Apr. 4, 2006

(86) PCT No.: PCT/EP2006/003035
§ 371 (c)(1),
(2), (4) Date: Oct. 7, 2009

(87) PCT Pub. No.: WO2006/117048
PCT Pub. Date: Nov. 9, 2006

(65) Prior Publication Data
US 2010/0016529 A1    Jan. 21, 2010

(30) Foreign Application Priority Data
Apr. 29, 2005 (EP) .................... 05009441

(51) Int. Cl.
*C08F 4/80* (2006.01)
*C08F 4/70* (2006.01)
*C08F 110/02* (2006.01)
*C07F 15/02* (2006.01)

(52) U.S. Cl. .............. 526/169.1; 526/169; 526/161; 526/172; 526/352; 556/138

(58) Field of Classification Search ............ 556/138; 526/169.1, 161, 172, 352
See application file for complete search history.

(56) References Cited

U.S. PATENT DOCUMENTS
6,063,881 A * 5/2000 Bennett ................ 526/161
(Continued)

FOREIGN PATENT DOCUMENTS
CN    1322717 A    * 11/2001
(Continued)

OTHER PUBLICATIONS
Schmidt et al., J. Appl. Polym. Sci., 2003, 88, 476-482.*
(Continued)

*Primary Examiner* — Rip A. Lee
(74) *Attorney, Agent, or Firm* — Cantor Colburn LLP

(57) ABSTRACT

The present invention relates to a catalyst precursor for the production of odd olefins having the formula:

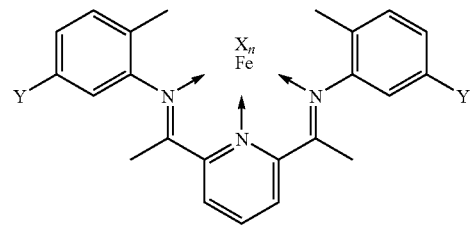

wherein X and Y are halogen and n is 2 or 3; and to a process for its preparation and a method for oligomerization of ethylene.

15 Claims, 3 Drawing Sheets

U.S. PATENT DOCUMENTS 6,461,994 B1 * 10/2002 Gibson et al. .................. 502/155

FOREIGN PATENT DOCUMENTS

| CN | 1421467 A | * | 6/2003 |
| CN | 1621423 A | * | 6/2005 |
| EP | 1 125 928 A9 | | 8/2001 |
| JP | 2003-147009 A | * | 5/2003 |
| WO | WO 2005/103100 A1 | * | 11/2005 |

OTHER PUBLICATIONS

Schmidt et al., J. Mol. Catal. A: Chemical, 2004, 222, 9-15.*
Wang et al., Gaofenzi Xuebao, 2005, 1, 132-136.*
Zhang et al., J. Mol. Catal. A: Chemical, 2005, 230, 1-8.*
Li et al., Heibei Gongye Daxue Xuebao, 2004, 33, 33-37.*
Zhang et al., J. Mol. Catal. A: Chemical, 2004, 219, 249-254.*
Huang et al., Gaofenzi Xuebao, 2004, 1, 125-128.*
Zhang et al., Gaofenzi Xuebao, 2005, 2, 191-196.*
Cao, et al., Shiyou Huagong, 2003, 32(8), 678-681.*

"Iron(II)-based Catalysts for Ethene Oligomerization"; Schmidt et al.; J. of Applied Polymer Science; vol. 88, p. 476-482 (2003).
"N,N,N-Tridentate Iron(II) and Vanadium(III) Complexes, Part I. Synthesis and Characterization"; Schimdt et al., J. of Molecular Catalysis, A: Chemical; vol. 222; p. 9-15(2004).
"Iron-Based Catalysts with Exceptionally High Activities and Selectivities for Oligomerization of Ethylene . . . ";Small et al.;J.Am. Chem. Soc.;vol. 120; No. 28;p. 7143-7144 (1998).
"Late-Metal Catalysts for Ethylene Homo- and Copolymerization"; Ittel et al.;Chem. Rev.; vol. 100; No. 4; p. 1169-1203 (2000).
"Oligomerisation of Ethylene by Bis(imino)pyridyliron and -cobalt Complexes"; Britovsek et al.; Chem.Eur.J.; vol. 6; No. 12; p. 2221-2231(2000).
"Iron and Cobalt Ethylene Polylmerization Catalysts Bearing 2,6-Bis(Imino)Pyridyl Ligands: . . . ";Britovsek et al.; J. Am. Chem. Soc.; vol. 121; p. 8728-8740 (1999).
Britovsek et al. "Novel Olefin Polymerization Catalysts Based on Iron and Cobalt", Chemical Communications, 1998, p. 845-850.

* cited by examiner

CATALYST PRECURSOR FOR THE PRODUCTION OF OLEFINS WITH AN ODD NUMBER OF CARBONS ATOMS, PROCESS FOR ITS PREPARATION AND PRODUCTION METHOD FOR SUCH OLEFINS

CROSS-REFERENCE TO RELATED APPLICATIONS

This application is a national phase filing of International Application PCT/EP2006/003035, filed Apr. 4, 2006, claiming priority to European Patent Application 05009411.6, filed on Apr. 29, 2005.

The present invention relates to a catalyst precursor for the production of odd olefins, a process for its preparation as well as to a method for the production of odd olefins using that catalyst precursor.

Processes for the oligomerization of ethylene or other olefins are well known in the prior art. For example, coordination compounds of iron halides with 2,6-diiminopyridines have been reported to be precatalysts for the polymerization and oligomerization of ethylene, see Small, B. L.; Brookhart, M. *Journal of the American Chemical Society* 1998, 120, 7143-7144; and Birtovsek, G. J. P.; Gibson, V.; Kimberley, B. S.; Maddox, P. J.; McTavish, S. J.; Solan, G. A.; White, A. J. P.; Williams, D. J. *Chemical Communications (Cambridge)* 1998, 849-850.

Further, olefins with odd numbers of carbon atoms, e.g. 1-heptene, 1-nonene, 1-undecene or 1-tridecene are valuable chemical intermediates for the synthesis of various compounds. Up to now such odd numbered olefins are mainly isolated from natural products or are produced in small amounts as side products of commercial procedures for the production of oligomers with even numbers of carbon atoms, e.g. the SHOP process.

It is therefore an object of the present invention to overcome the disadvantages of the prior art and to provide a catalyst composition which may be utilized in an oligomerization process of ethylene for providing an increased amount of olefins having odd numbered carbon atoms. Further, it is an object of the present invention to provide a process for the preparation of that catalyst composition.

The object is achieved by a catalyst precursor for the production of odd olefins having the formula:

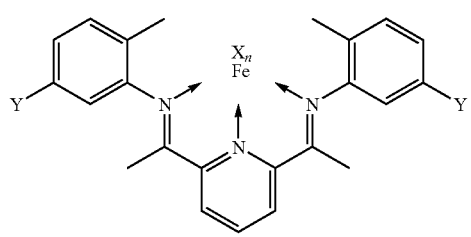

wherein X and Y are halogen and n is 2 or 3.

Preferably, X is chlorine and Y is fluorine, chlorine, bromine or iodine.

Additionally, a process for the preparation of the inventive catalyst precursor is provided comprising the steps of:
(i) reacting 2,6-diacetylpyridine with a suitably substituted aniline to prepare a 2,6-diiminopyridine according to the following scheme:

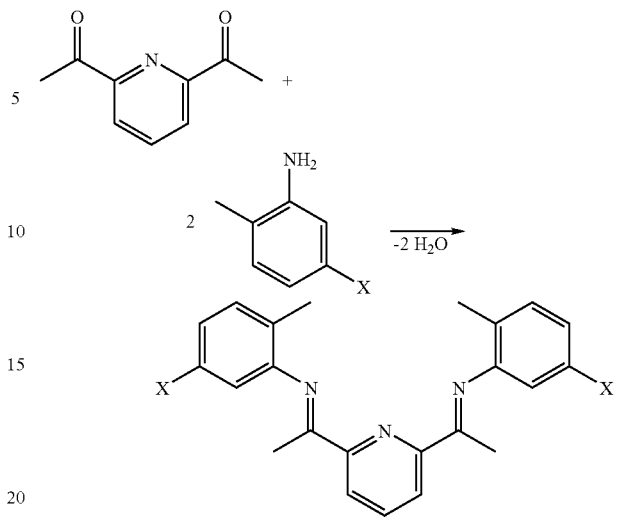

reacting the 2,6-diiminopyridine obtained in step (i) with iron halide according to the scheme:

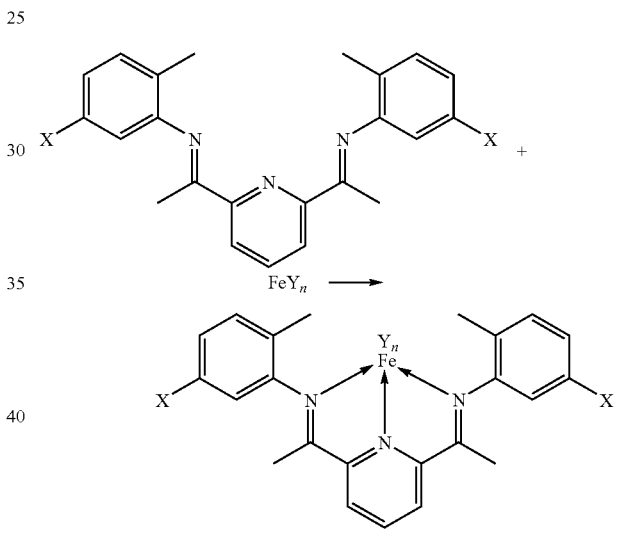

Preferably, step (i) and (ii) are carried out in an inert solvent, such as toluene, n-butanol, methylene dichloride or diethyl ether.

More preferably, the oxidation state of the iron in the iron halide is +2 or +3.

Additionally, a method for the production of odd olefins is provided, comprising the steps of:
(a) activating the inventive catalyst precursor with an activator; and
(b) oligomerizing ethylene with the activated catalyst precursor obtained in step (a).

Preferably, the activator is an alkyl aluminum, methyl aluminoxane, modified methyl aluminoxane, borate or a superacid.

More preferably, the activator is an aluminum compound and the ratio of aluminum to iron is from about 50 to about 10000, preferably from about 200 to about 3000.

In one embodiment, the oligomerization temperature is from about −100 to about 300° C., preferably from about −10 to about 100° C.

The oligomerization may be carried out in an inert solvent, such as toluene and/or pentane.

Finally, the ethylene pressure may be preferably from about 0.1 to about 60 bar, preferably from about 0.5 to about 10 bar.

Surprisingly, it was found that in a process for the oligomerization of ethylene using the catalyst precursor according to the invention olefinic oligomers may be obtained having a significantly high amount of odd numbered olefins incorporated.

Further, depending on the specific catalyst precursor chosen and on the specific reaction conditions, the ratio of oligomers with odd and even numbers of carbon atoms may be optimized.

Additional features and advantages of the subject-matter of the present will become apparent for someone skilled in the art upon reading the following detailed description and examples section in conjunction with the accompanying drawings, wherein.

The following abbreviations are used:
FW=formula weight
GC=gas chromatography
GC/MS=gas chromatography followed by mass spectrometry
NMR=nuclear magnetic resonance
RT=room temperature
MeOH=methanol
EtOH=ethanol
THF=tetrahydrofurane

EXAMPLE 1

2,6-bis-[1-(5-chloro-2-methylphenylimino)-ethyl]-pyridine

In a 25 ml round bottom flask 3 g of 2,6-diacetylpyridine (FW 163.13, 18.4 mmol) and 100 ml of toluene were placed. Next a few milligrams of p-toluenesulfonic acid were added followed by 7.81 g of 5-chloro-2-methyl-aniline (FW 141.60, 55.2 mmol). The reaction mixture was heated under reflux at a Dean-Stark trap for 2 days and then cooled to room temperature. After neutralization with NaHCO$_3$ it was washed with water and the organic layer was separated using a separatory funnel. Na$_2$SO$_4$ was used to dry the toluene solution and the solvent was removed by distillation. The residue was recrystallized from EtOH yielding 5.88 g (78% yield) of pale yellow crystals. The product was subjected to GC/MS analysis:

MS m/e (%) 411 (39), 410 (36), 409 (57), 397 (20), 396 (70), 395 (54), 394 (100), 284 (13), 244 (15), 243 (15), 229 (16), 166 (23), 131 (14), 125 (32), 89 (26)

Figure 1:
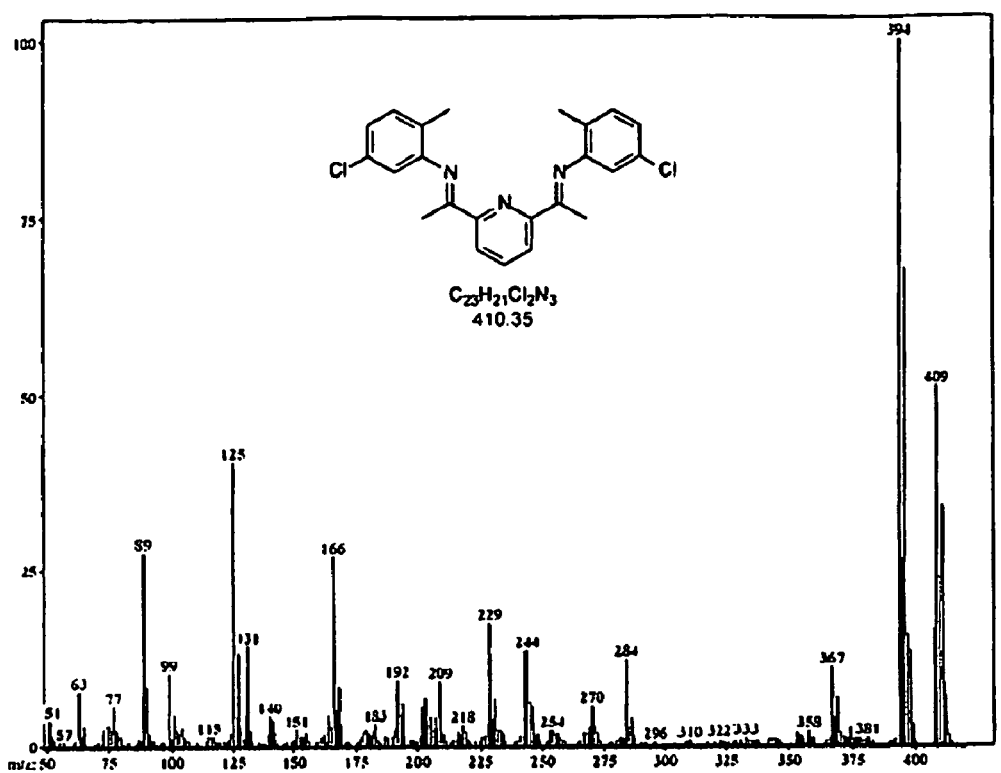
FIG. 1 is a mass spectrum of 2,6-bis[1-(5-chloro-2-methylphenylimino)-ethyl]-pyridine.

The mass spectrum of the compound is given in FIG. 1. Further, $^1$H and $^{13}$C NMR spectra were collected:

$^1$H NMR (ppm, CDCl$_3$) 8.36 (d, 2H), 7.91 (t, 1H), 7.19 (d, 2H), 6.99 (d, 2H), 6.69 (d, 2H), 2.32 (s, 6H), 2.11 (s, 6H)

$^{13}$C NMR (ppm, CDCl$_3$) 167.6, 155.1, 151.2, 132.2, 125.4, (C$_q$); 137.0, 131.0, 123.3, 122.5, 119.4, (CH); 16.5, 14.7, (CH$_3$)

Figure 2:
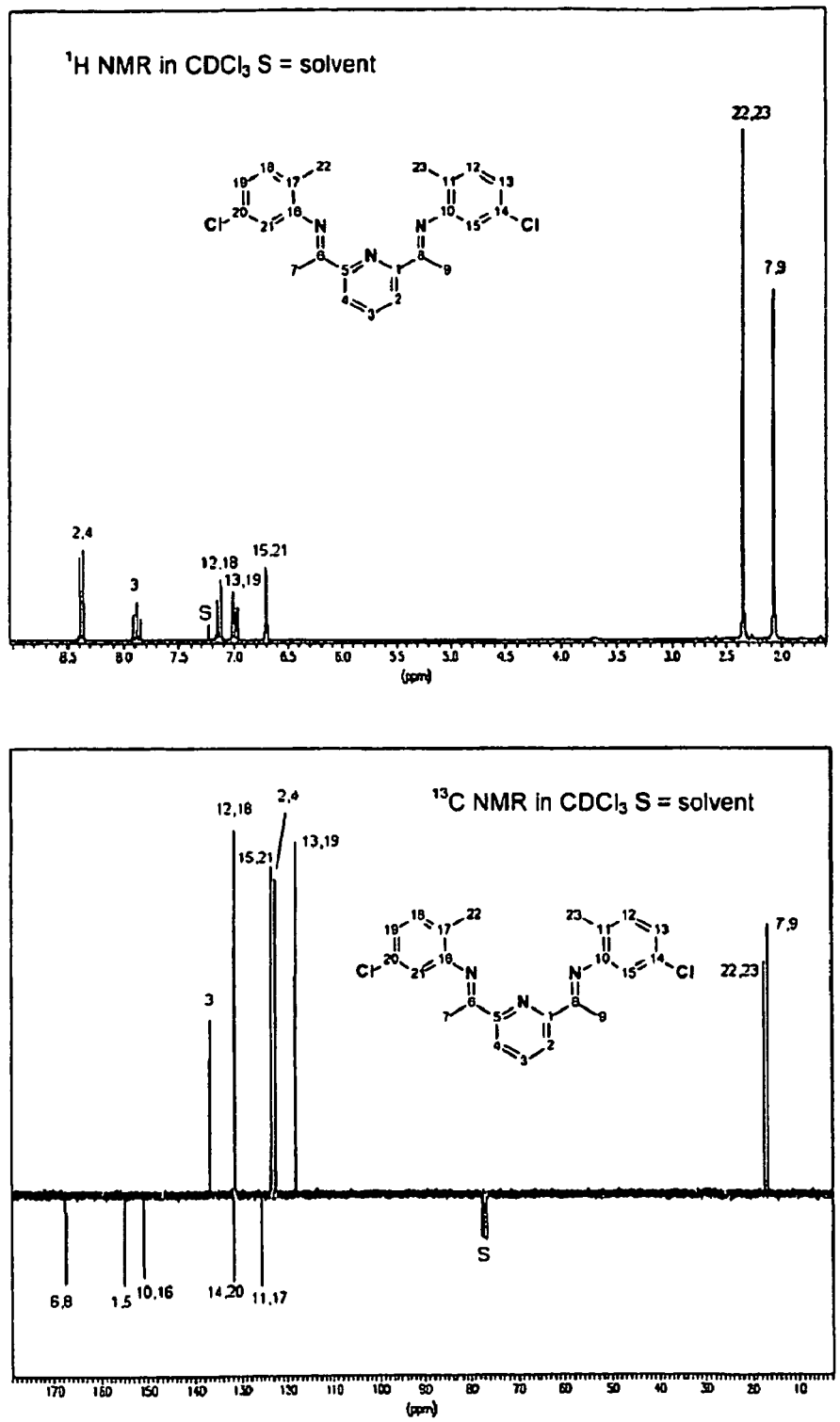
FIG. 2 are $^1$H and $^{13}$C NMR spectra of 2,6-bis-[1-(5-chloro-2-methylphenylimino)-ethyl]-pyridine.

The $^1$H and $^{13}$C NMR spectra are given in FIG. 2.

Further, after recrystallization from diethyl ether suitable crystals for X ray analysis have been obtained and the following crystal data have been received.

| Crystal data | |
|---|---|
| crystal system | monoclinic |
| space group | P 21/c |
| unit cell | a = 11.1358(22) Å |
| | b = 15.7676(18) Å |
| | c = 12.3067(16) Å |
| | β = 95.88(1)° |
| density (calc.) | 1.268 g/cm$^3$ |
| Selected bond lengths | |
| C5-C6 = 1.497(2) | C1-C15 = 1.500(1) |
| C6-N2 = 1.271(0) | C15-N3 = 1.264(2) |
| N2-C8 = 1.425(2) | N3-C17 = 1.426(1) |
| Torsion angles | |
| C6-N2-C8-C14 | −81.42(1) |
| C15-N3-C17-C23 | 91.47(1) |

Figure 3:
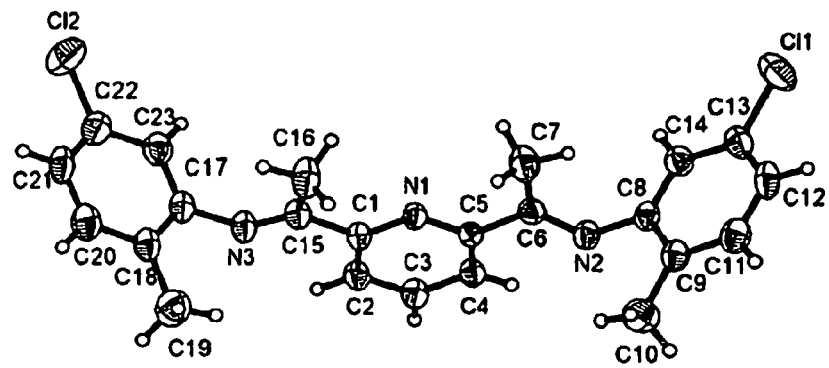
FIG. 3 shows a structure obtained by X ray analysis of 2,6-bis-[1-(5-chloro-2-methylphenylimino)-ethyl]-pyridine.

The crystal data obtained result in the structure of the compound given in FIG. 3.

EXAMPLE 2

2,6-bis-[1-(5-bromo-2-methylphenylimino)-ethyl]-pyridine

In a 25 ml round bottom flask 3 g of 2,6-diacetylpyridine (FW 163.13, 18.4 mmol) and 100 ml of toluene were placed. Next a few milligrams of p-toluenesulfonic acid were added followed by 10.27 g of 5-bromo-2-methyl-aniline (FW 186.05, 55.2 mmol). The reaction mixture was heated under reflux at a Dean-Stark trap for 8 h and then cooled to room temperature. After neutralization with NaHCO$_3$ it was washed with water and the organic layer was separated using a separatory funnel. Na$_2$SO$_4$ was used to dry the toluene solution and the solvent was removed by distillation. The residue was recrystallized from MeOH yielding 3.76 g (41% yield) of pale yellow crystals. The product was subjected to GC/MS analysis.

Retention time=918s

MS m/e (%) 501 (26), 500 (20), 499 (51), 497 (26), 486 (53), 485 (26), 484 (100), 482 (52), 210 (16), 171 (16), 169 (18), 90 (24), 89 (16)

EXAMPLE 3

[2,6-bis-[1-(5-chloro-2-methylphenylimino)-ethyl]-pyridine]iron(II)dichloride

A Schlenk tube (250 ml) was evacuated and filled with argon three times. It was filled with 80 ml of dry n-butanol and 0.501 g 2,6-bis-[1-(5-chloro-2-methylphenylimino)-ethyl]-pyridine (FW 410.35, 1.2 mmol) were dissolved in it. Dry iron(II)dichloride (FW 126.75, 0.154 g, 1.2 mmol) was added and the color changed immediately from yellow to blue. The reaction mixture was stirred at room temperature for one hour and then the precipitate was filtered under inert gas. The residue was washed with pentane and dried under vacuum yielding 0.63 g (96% yield). The product was characterized by mass spectrometry:

MS m/e (%) 411 (34), 410 (21), 409 (48), 408 (18), 396 (62), 395 (23), 394 (100), 296 (51), 244 (23), 243 (19), 229 (22), 166 (32), 131 (17), 125 (32), 89 (18)

Figure 4:
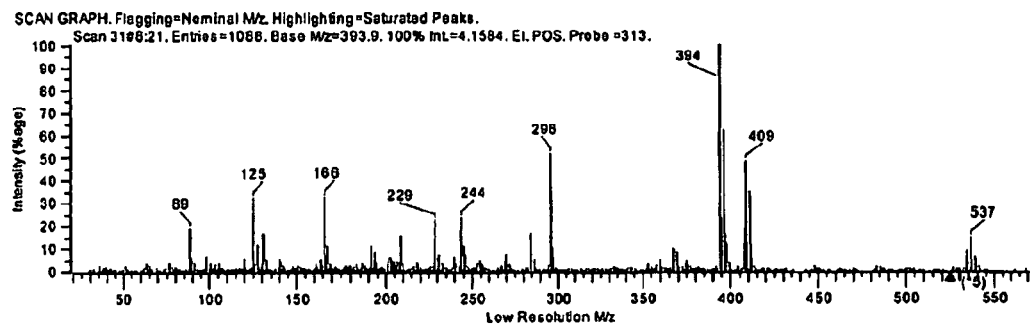
FIG. 4 is a mass spectrum of [2,6-bis-[1-5-(chloro-2-methylphenylimino)-ethyl]-pyridine]iron(II)dichloride.

The mass spectrum for the catalyst precursor according to example 3 is given in FIG. 4.

EXAMPLE 4

[2,6-bis-[1-(5-chloro-2-methylphenylimino)-ethyl]-pyridine]iron(II)dibromide

A Schlenk tube (250 ml) was evacuated and filled with argon three times. It was filled with 80 ml of dry n-butanol and 0.500 g 2,6-bis-[1-(5-chloro-2-methylphenylimino)-ethyl]-pyridine (FW 410.35, 1.2 mmol) were dissolved in it. Dry iron(II)dibromide (FW 213.77, 0.256 g, 1.2 mmol) was added and the color changed immediately from yellow to blue. The reaction mixture was stirred at RT for one hour and then the precipitate was filtered under inert gas. The residue was washed with pentane and dried under vacuum yielding 0.68 g (90% yield). The product was characterized by mass spectrometry:

MS m/e (%) 546 (20), 411 (32), 410 (23), 409 (46), 396 (68), 395 (26), 394 (100), 244 (25), 243 (28), 229 (34), 209 (18), 166 (35), 131 (27), 125 (42), 89 (26), 44 (31)

EXAMPLE 5

Oligomerization using [2,6-bis-[1-(5-chloro-2-methylphenylimino)-ethyl]-pyridine]iron(II)dibromide as catalyst precursor A Schlenk tube was filled with 150 ml of toluene and 0.068 g of [2,6-bis-[1-(5-chloro-2-methylphenylimino)-ethyl]-pyridine]iron(II)dibromide (FW 625.99, 0.11 mmol) was added. The cocatalyst MAO was added (11.6 ml, Al:Fe=500:1) and the Schlenk tube was pressurized with 1 bar of ethylene. The reaction was carried out at RT for an hour and the activity was determined by measuring the weight gained after releasing the pressure. After that the mixture was cooled to 0° C. and hydrolyzed by adding water. The organic layer was separated, dried over $Na_2SO_4$ and subjected to GC analysis.

The resulting activity was 2480 g(PE)/g(Fe)*$h^{-1}$ and the amount of oligomers with odd numbers of carbon atoms was approximately 19%.

EXAMPLE 6

Oligomerization using [2,6-bis-[1-(5-bromo-2-methylphenylimino)-ethyl]-pyridine]iron(II)dichloride as catalyst precursor A Schlenk tube was filled with 150 ml of toluene and 0.0176 g of [2,6-bis-[1-(5-bromo-2-methylphenylimino)-ethyl]-pyridine]iron(II)dichloride (FW 625.99, 0.028 mmol) was added. The cocatalyst MAO was added (4.3 ml, Al:Fe=750:1) and the Schlenk tube was pressurized with 1 bar of ethylene. The reaction was carried out at 0° C. for an hour and the activity was determined by measuring the weight gained after releasing the pressure. After that the mixture was hydrolyzed by adding water. The organic layer was separated, dried over $Na_2SO_4$ and subjected to GC analysis.

The resulting activity was 2980 g(PE)/g(Fe)*$h^{-1}$ and the amount of oligomers with odd numbers of carbon atoms was approximately 6%.

As can be seen, using the catalyst precursors according to the present invention in a method for oligomerization of ethylene may result in significant amounts of oligomers with odd numbers of carbon atoms.

So far, no other catalyst precursor is known that produces odd olefins from ethylene in that high amount.

The features disclosed in the foregoing description, in the claims and/or in the accompanying drawings may, both separately and in any combination thereof, be material for realizing the invention in diverse forms thereof.

The invention claimed is:

1. A catalyst precursor for the production of odd olefins having the formula:

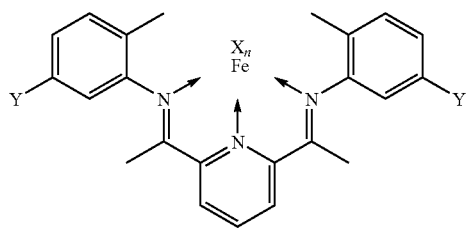

wherein X is bromine and Y is chlorine, or X is chlorine and Y is bromine, and n is 2 or 3.

2. A process for the preparation of a catalyst precursor having the formula:

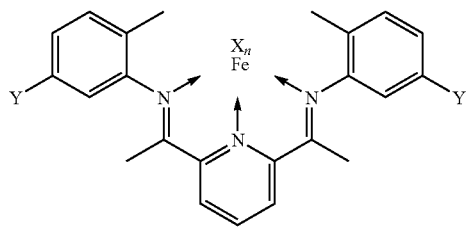

wherein X is bromine and Y is chlorine, or X is chlorine and Y is bromine, and n is 2 or 3 comprising the steps of:

(i) reacting 2,6-diacetylpyridine with a suitably substituted aniline to prepare a 2,6-diiminopyridine according to the following scheme:

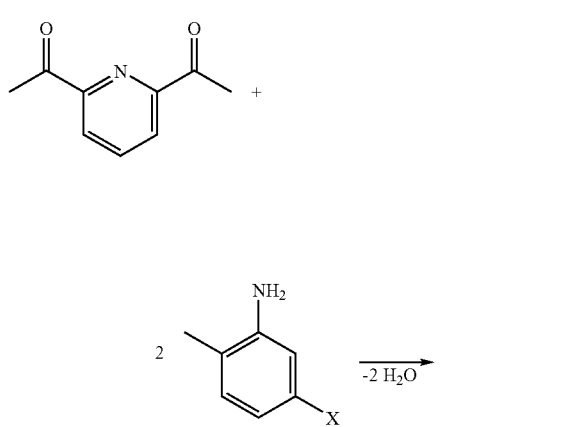

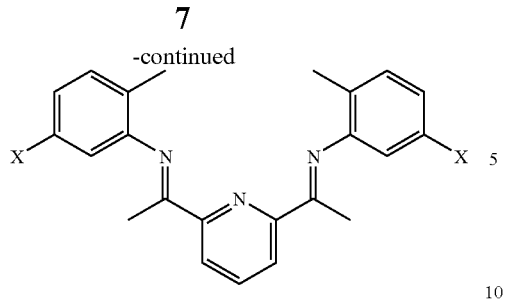

(ii) reacting the 2,6-diiminopyridine obtained in step (i) with iron halide according to the scheme:

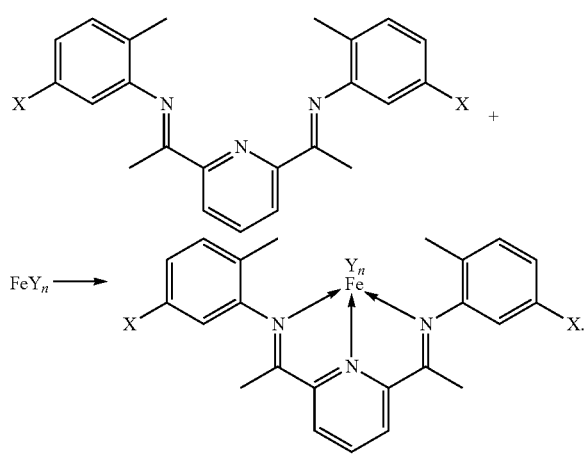

3. The process according to claim 2 wherein step (i) and (ii) are carried out in an inert solvent.

4. The process according to claim 3, wherein the inert solvent is toluene, n-butanol, methylene dichloride or diethyl ether.

5. The process according claim 2 wherein the oxidation state of the iron in the iron halide is +2 or +3.

6. A method for the production of odd olefins comprising the steps of:
(a) activating the catalyst precursor having the formula:

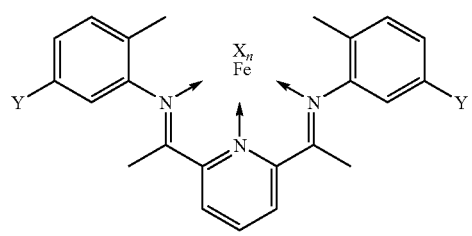

wherein X is bromine and Y is chlorine, or X is chlorine and Y is bromine, and n is 2 or 3
with an activator; and
(b) oligomerizing ethylene with the activated catalyst precursor obtained in step (a).

7. The method according to claim 6 wherein the activator is an alkyl aluminum, methyl aluminoxane, modified methyl aluminoxane, borate or a superacid.

8. The method according to claim 6 wherein the activator is an aluminum compound and the ratio of aluminum to iron is from about 50 to about 10000.

9. The method according to claim 8 wherein the ratio of aluminum to iron is from about 200 to about 3000.

10. The method according to claim 6 wherein the oligomerization temperature is from about −100 to about 300° C.

11. The method according to claim 10 wherein the oligomerization temperature is from about −10 to about 100° C.

12. The method according claim 6, wherein the oligomerization is carried out in an inert solvent.

13. The method according to claim 12, wherein the inert solvent is toluene and/or pentane.

14. The method according to claim 6, wherein the ethylene pressure is from about 0.1 to about 60 bar.

15. The method according to claim 14, wherein the ethylene pressure is from about 0.5 to about 10 bar.

* * * * *